US008273331B2

(12) United States Patent
Zeng

(10) Patent No.: US 8,273,331 B2
(45) Date of Patent: Sep. 25, 2012

(54) INHALATION COMPOSITIONS

(75) Inventor: Xian-Ming Zeng, Surrey (GB)

(73) Assignee: Norton Healthcare Ltd., London (GB)

( * ) Notice: Subject to any disclaimer, the term of this patent is extended or adjusted under 35 U.S.C. 154(b) by 937 days.

(21) Appl. No.: 10/646,361

(22) Filed: Aug. 21, 2003

(65) Prior Publication Data

US 2004/0258626 A1    Dec. 23, 2004

(30) Foreign Application Priority Data

Aug. 21, 2002  (GB) .................................. 0219513.9
Aug. 21, 2002  (GB) .................................. 0219514.7

(51) Int. Cl.
*A61K 9/14*       (2006.01)
*A61K 9/12*       (2006.01)
*A61K 9/00*       (2006.01)

(52) U.S. Cl. .......................................... 424/46; 424/489

(58) Field of Classification Search .................. 424/489, 424/46

See application file for complete search history.

(56) References Cited

U.S. PATENT DOCUMENTS

| 3,957,965 | A | 5/1976 | Hartley et al. | |
|---|---|---|---|---|
| 3,994,974 | A | 11/1976 | Murakami et al. | |
| 4,937,254 | A | 6/1990 | Sheffield et al. | |
| 5,684,199 | A | 11/1997 | Francotte | |
| 6,017,963 | A | 1/2000 | Alfonso et al. | |
| 6,030,604 | A | 2/2000 | Trofast | |
| 6,071,971 | A | 6/2000 | Senanayake | |
| 6,199,607 | B1 | 3/2001 | Trofast | |
| 6,284,287 | B1 | 9/2001 | Sarlikiotis et al. | |
| 6,616,914 | B2* | 9/2003 | Ward et al. | 424/45 |
| 6,645,466 | B1* | 11/2003 | Keller et al. | 424/43 |
| 6,737,044 | B1* | 5/2004 | Dickinson et al. | 424/46 |
| RE38,912 | E | 12/2005 | Walz et al. | |
| 7,090,870 | B1 | 8/2006 | Vanderbist et al. | |
| 2001/0041164 | A1 | 11/2001 | Verkerk et al. | |
| 2002/0018753 | A1 | 2/2002 | Blondino et al. | |
| 2002/0103260 | A1 | 8/2002 | Clarke et al. | |
| 2002/0106332 | A1 | 8/2002 | Walz et al. | |
| 2002/0110529 | A1 | 8/2002 | Bechtold-Peters et al. | |
| 2003/0133880 | A1 | 7/2003 | Musa et al. | |
| 2003/0180283 | A1* | 9/2003 | Batycky et al. | 424/130.1 |
| 2005/0158248 | A1 | 7/2005 | Zeng | |
| 2006/0029552 | A1 | 2/2006 | Staniforth | |
| 2006/0292083 | A1* | 12/2006 | Zeng | 424/46 |
| 2008/0131518 | A1 | 6/2008 | Zeng | |

FOREIGN PATENT DOCUMENTS

| WO | WO 01/39745 | 6/1992 |
|---|---|---|
| WO | WO-98/31352 | 7/1998 |
| WO | WO-98/31353 | 7/1998 |
| WO | 98/50015 A1 | 11/1998 |
| WO | WO 99/51205 * | 10/1999 |
| WO | WO-00/28979 | 5/2000 |
| WO | WO-00/48587 A | 8/2000 |
| WO | WO-00/53157 A | 9/2000 |
| WO | WO-00/53158 A | 9/2000 |
| WO | WO 92/10229 | 6/2001 |
| WO | WO-01/89491 A | 11/2001 |

OTHER PUBLICATIONS

"Spray Performance Considerations," accessed on Sep. 7, 2011 at www.spray.com/cat70/cat70pdf/ssco_cat70_a60.pdf.*
Goodman and Gilman's The Pharmacological Basis of Therapeutics, 10th Ed., McGraw Hill Companies Inc., New York 2001, pp. 1701-1704.
Gennaro, "Pharmaceutical Necessities", Remington's Pharmaceutical Sciences 18th Ed., MACK Publishing Co., Easton PA1990, pp. 1286-1329.
Gennaro, "Oral Solid Dosage Forms", Remington's Pharmaceutical Sciences 18th Ed., MACK Publishing Co., Easton PA1990, pp. 1635-1638.
O'Connor et al, "Powders", Remington: The Science and Practice of Pharmacy, 19th Ed., Lippincott, Williams & Wilkins1995, pages.
Zeng et al, "Carrier Particles", Particulate Interactions in Dry Podwer Formulations for Inhalation, Taylor & Francis 2001 pp. 144-151.
DMV-Fonterra Excipients: "Pharmatose, milled and sieved lactose." Online Retrieved from the Internet: URL:http://www.dmv-fonterra-excipients.com/products/~/media/DBF13799A281431DB94DB5C36CCC48B7.ashx, retrieved on May 25, 2009.
Xian Ming Zeng et al., "The Influence of Lactose Carrier on the Content Homogeneity and Dispersibility of Beclomethasone Dipropionate From Dry Powder Aerosols", International Journal of Pharmaceutics, Elsevier BV, NL., vol. 197, No. 1/02, Jan. 1, 2000, pp. 41-52, XP001031575, ISSN: 0378-5173.
Carius W, "Process Monitoring With High-Shear High Intensity Mixers/Power Consumption Measurement in Pilot Plant Laboratory", Pharmazeutische Industrie 1992 DE, vol. 54, No. 6, 1992, pp. 543-546, XP002529165, ISSN: 0031-711X.
Vippagunta et al. "Crystalline Solids," Advanced Drug Delivery Reviews, 2001, 48, pp. 18.

* cited by examiner

*Primary Examiner* — James H. Alstrum-Acevedo
(74) *Attorney, Agent, or Firm* — RatnerPrestia

(57) ABSTRACT

The invention provides a dry powder inhalation composition comprising medicament particles and a mixture of lactose particles with a VMD of between about 70 and about 120 microns and a diameter of less than 250 microns, the mixture being characterized in that up to 96% by weight of the lactose particles are less than 150 microns in diameter and wherein up to 25% by weight of the lactose particles are less than 5 microns in diameter. The compositions provide for a more accurate, uniform and consistent dispersion when used with, for example, a multidose dry powder inhaler. Also disclosed are methods for use of the compositions of the invention.

15 Claims, 3 Drawing Sheets

INHALATION COMPOSITIONS

CROSS-REFERENCE TO RELATED APPLICATIONS

This application claims priority to United Kingdom Patent Application No.: 0219514.7 filed on Aug. 21, 2002 and United Kingdom Patent Application No 0219513.9 filed on Aug. 21, 2002.

TECHNICAL FIELD OF THE INVENTION

This invention relates to dry powder inhalation compositions, their preparation and use. In particular, it is concerned with formulations of the medicament formoterol and pharmaceutically acceptable derivatives thereof mixed with particulate lactose.

BACKGROUND OF THE INVENTION

In order to be able to be inspired into the key target sites in the lungs of patients, inhalation drugs are typically provided in micronized form with average particle sizes of up to 10 microns. A number of devices have been developed for assisting the delivery of such medicaments into the lungs of patients. In one sort of device, a dry powdered inhaler (DPI) device, the medicament to be inhaled is dispensed into an air stream produced by the inspiratory action of the patient. A large number of such devices have been developed. The device may be a single dose device (e.g., wherein drug is dispensed from a pre-metered dosage means such as a capsule) or multidose (where the drug is stored in a reservoir and then metered prior to dispersal in the air stream or where the drug is pre-metered and then stored in multiple dosage packs such as blisters). In a number of DPI devices, the particulate drug is mixed with an excipient powder of larger average particle size and the drug particles are blended with the excipient to create a generally homogenous mixture. The larger particle size of the excipient results in the powder mixture being flowable, and the homogeneity of the mixture enable it to be metered into accurately measurable doses. This is of particular importance when only very small quantities of the drug are required in a dose. Excipient powders of this kind and pharmaceutical powder compositions for inhalation utilizing such excipients are described, for example, in U.S. Pat. No. 3,957,965.

The accurate metering of highly potent inhalant drugs causes particular problems, as the quantity of medicament in the composition relative to that of the carrier is likely to be particularly small (less than 1 part of drug to 50 parts of carrier). This is exemplified by the medicament formoterol, which is often administered to patients at a dose of less than 60 micrograms (doses may be as small as 6 micrograms).

U.S. Pat. No. 6,199,607 to Trofast describes a multi-step process for preparing a dry powder formoterol composition. The process as described includes the mixing of the components followed by micronization of the blend. The micronized particles were subsequently treated to remove amorphous areas in their crystal structure. The particles are then agglomerated, sieved, and spheronized, followed by a second sieving, spheronization and sieving.

What are needed then are simple methods for producing dry powder medicaments while maintaining desirable flow and deposition characteristics following dispersion.

SUMMARY OF THE INVENTION

The invention provides compositions for the dry powder inhalation of medicament comprising particulate medicament and a lactose carrier of defined particulate sizes and proportions. The compositions provide for an accurate, uniform and consistent dispersion when used with, for example, a multidose dry powder inhaler. Also disclosed are methods for use of the compositions of the invention.

Hence, dry powder inhalation compositions of a particulate medicament (e.g., formoterol) and lactose of defined particulate size and proportions are described which are easier to handle, and can be readily filled into the reservoir of a multidose dry powder inhaler (MDPI), (see, for example, WO 92/10229). Additionally, these compositions are more accurately metered and provide more uniform and consistent dispersions when dispensed by MDPI devices. Certain compositions may also be more stable.

One aspect of the invention provides a dry powder inhalation composition comprising medicament particles and a mixture of lactose particles with a VMD of between about 70 and about 120 microns and a diameter of less than 250 microns, the mixture being characterized in that up to 96% by weight of the lactose particles are less than 150 microns in diameter and wherein up to 25% by weight of the lactose particles are less than 5 microns in diameter.

Another aspect of the invention provides for a multidose dry powder inhaler comprising the composition according to the invention.

An aspect of the invention provides methods for the administration of a particulate medicament, comprising inhalation of a composition of the invention from a multidose dry powder inhaler, are provided.

In another aspect, the invention provides a method for the administration of a therapeutically effective amount of compositions prepared by the processes of the invention, for the treatment of conditions responsive to the medicaments of choice.

DETAILED DESCRIPTION OF THE INVENTION

Figure 1:
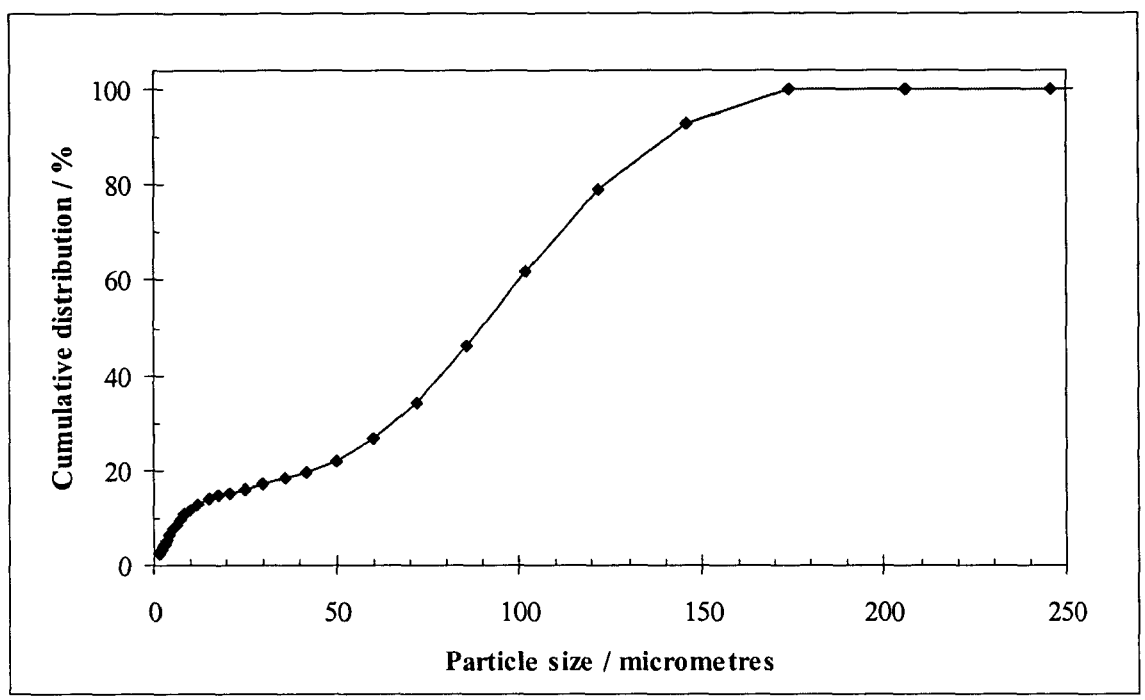
FIG. 1: Graphical representation of particle size distribution for lactose particles.

The invention provides compositions for the dry powder inhalation of medicament comprising particulate medicament and a lactose carrier of defined particulate sizes and proportions. The compositions provide for a more accurate, uniform and consistent dispersion when used with, for example, a multidose dry powder inhaler. Also disclosed are methods for use of the compositions of the invention.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10*th* Ed., McGraw Hill Companies Inc., New York (2001).

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used in this specification, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

As used herein, unless specifically indicated otherwise, the word "or" is used in the "inclusive" sense of "and/or" and not the "exclusive" sense of "either/or."

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

One aspect of the invention provides a dry powder inhalation composition comprising medicament particles and a mixture of lactose particles with a volume mean diameter (VMD) of between about 70 and about 120 microns and a diameter of less than 250 microns, the mixture being characterized in that up to 96% by weight of the lactose particles are less than 150 microns in diameter and wherein up to 25% by weight of the lactose particles are less than 5 microns in diameter.

In one embodiment, up to 85% by weight of the lactose particles are less than 90 microns in diameter, whereas in another embodiment up to 37% by weight of the lactose particles are less than 60 microns in diameter.

In yet another embodiment, up to 35% by weight of the lactose particles are less than 30 microns in diameter, while in still other embodiments up to 31.5% by weight of the lactose particles are less than 15 microns in diameter.

In other embodiments of this aspect, up to 30% by weight of the lactose particles are less than 10 microns in diameter, and in some embodiments between 6.5 and 24.5% by weight of the lactose are less than 5 microns in diameter.

In some embodiments of this aspect, the composition comprises up to 10% by weight of medicament. In other embodiments, the medicament is formoterol or a pharmaceutically derivative or salt thereof. In some cases the medicament is formoterol fumarate dihydrate.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

As used herein, "up to", when used in conjunction with a percentage of lactose particulates of a named size, is meant to require the presence of an amount other than zero of particles of the named size and that the named numeric percentage is the upper limit for the presence of particles of the named size.

Another aspect of the invention provides for a multidose dry powder inhaler comprising a composition according to the invention.

Another aspect of the invention provides a method for the administration of a particulate medicament, comprising inhalation from and MDI of a dry powder inhalation composition of the invention.

The compositions according to the invention are optionally formulated in a pharmaceutically acceptable vehicle with any of the well-known pharmaceutically acceptable medically inert moiety such as carriers, including diluents, excipients, surfactants, and flavourings (see *Remington's Pharmaceutical Sciences*, 18*th* Ed., Gennaro, Mack Publishing Co., Easton, Pa. 1990 and *Remington: The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. See also Zeng, et al. *Particulate Interactions in Dry Powder Formulations of Inhalation*, Taylor & Francis, London, 2001.

As used herein, "medicament" or "active ingredient" is meant to encompass active pharmaceuticals appropriate for inhalation therapy in dry powder form. Representative, non-limiting examples include bronchodilators (e.g., epinephrine, metaproterenol, terbutaline, albuterol, and the like), anticholinergic agents (e.g., ipratropium bromide), xanthines (e.g., dyphylline, aminophylline), inhalant corticosteroids (e.g., flunisolide, beclomethasone, budesonide, and the like), or β-2 adrenergic receptor agonists (e.g., salmeterol and formoterol).

The medicament may be in any isomeric form or mixture of isomeric forms, for example a pure enantiomer, particularly the R, R-enantiomer, a mixture of enantiomers, a racemate or a mixture thereof (e.g., formoterol). Pharmaceutically acceptable derivatives of formoterol include pharmaceutically acceptable salts, in particular acid addition salts with inorganic acids such as hydrochloric acid, hydrobromic acid, sulphuric or phosphoric acid. The salt may also be with an organic acid such as acetic, succinic, maleic, furmaric, citric, tartaric, lactic or benzoic. The active ingredient and pharmaceutically acceptable derivatives thereof may exist in the form of a solvate, in particular a hydrate.

A form of active ingredient for use in the invention is formoterol fumarate, especially formoterol fumarate dihydrate, conveniently in its racemic form. Formoterol, salts and hydrates thereof and salt hydrates thereof as described above may be prepared by known methods, for example as described in U.S. Pat. No. 3,994,974 or U.S. Pat. No. 5,684,199.

In general, the medicament is present in the dry powder composition at an amount which is less than 10%, preferably less than 2% and most preferably less than 1% by weight of the composition. The actual amount of medicament in the composition will depend to a large extent on the nature of the dry powder inhaler and the quantity of composition that is metered for each individual dose. Where a large dose of composition is metered, the proportion of the medicament in the dose will be reduced. Particularly dilute compositions are disclosed in WO 01/39745, for example, 0.02% by weight.

In some embodiments, the mean particle diameter of the medicament is up to 10 microns in diameter, while in other embodiments, the mean particle size is up to 5 microns in diameter. In yet other embodiments, the mean particle size ranges from about 1 to about 5 microns in diameter. The particle size of the medicament can be reduced to the desired level by conventional means, for example by grinding in a mill, for example, an air jet, ball or vibrator mill, by sieving, by crystallization, by spray-drying or by lyophilization. Particle size may be determined using laser light scattering (Sympatec GmbH, Claasthal-Zellerfeld, Germany).

The desired particle size distribution of the lactose may be prepared in a similar way. However, it is preferable to prepare the lactose by blending two or more portions of previously prepared and classified lactose, for example a fine blend of lactose, in which the mean particle diameter is less than 10 microns in diameter and a portion in which the mean particle diameter is relatively coarse. A characteristic coarse lactose is supplied as classified lactose, which is collected on a mesh with mesh size of 63 microns, after passing through a mesh with mesh size of 90 microns.

The formulations of the compositions of the invention may conveniently be presented in unit dosage form and may be prepared by conventional pharmaceutical techniques. Such techniques include the step of bringing into association the compound of the invention and the pharmaceutically acceptable carrier(s), or an excipient. In general, the formulations are prepared by uniformly and intimately bringing into association the active ingredient with finely divided solid carriers, and then, if necessary, preparing discrete dosage units of the product.

The dry powder composition may be metered and filled into capsules, e.g., gelatin or hydroxypropyl methylcellulose capsules, such that the capsule contains a unit dose of medicament.

Doses of medicament to be used in accordance with the invention may range in general from 1 to 60 micrograms. When the medicament is formoterol fumarate dihydrate, the dose may range, for example, from 6 to 54 micrograms. Preferred doses are from 6 to 24 micrograms, especially the unit doses of 6 micrograms, 12 micrograms and 24 micrograms. These doses may be administered once or twice daily.

When the dry powder is in a capsule containing a unit dose of medicament, the total amount of composition will depend on the size of the capsules and the characteristics of the inhalation device with which the capsules are being used. However, representative characteristic total fill weights of dry powder to per capsule are between 1 and 25 mg, e.g., 5, 10, 15 or 20 mg.

Alternatively, the dry powder composition according to the invention may be filled into the reservoir of a multidose dry powder inhaler (MDPI), for example of the kind illustrated in WO 92/10229 (hereinafter referred to as the IVAX™ MDPI).

Compositions according to the invention may be readily prepared by blending the required amount of active ingredient with the required amount of particulate lactose of the desired particle size distribution. Preferably, the lactose is alpha lactose monohydrate.

In yet another aspect, the invention provides a method for the administration of a therapeutically effective amount of compositions prepared by the processes described herein, for the treatment of conditions responsive to the medicaments of choice. Non-limiting examples of conditions include chronic obstructive pulmonary disease, asthma, late phase allergic responses, or pulmonary inflammations.

The term "therapeutically effective amount" is used to denote treatments at dosages effective to achieve the therapeutic result sought. Furthermore, one of skill will appreciate that the therapeutically effective amount of the compositions of the invention may be lowered or increased by fine tuning and/or by administering more than one composition of the invention, or by administering a composition of the invention with another compound or composition. The invention therefore provides a method to tailor the administration/treatment to the particular exigencies specific to a given mammal.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Particle Size Distribution, Dose Delivery, and Fine Particle Fractions for a Formoterol Lactose Blend 0.265 grams of formoterol (as the fumarate dihydrate salt) was blended with 99.735 grams of lactose that has a particle size distribution within the range shown in Table 1. Blending was conducted using a tumbling mixing process (TURBULA™, Glen Creston, N.J., USA). The formoterol lactose blend was filled into the reservoir of an IVAX™ MDPI device.

TABLE 1

Particle size distributions for carrier lactose.
Median of particle size distribution must be in the range of 70-120 μm.

| | % Cumulative Undersize | |
| --- | --- | --- |
| Size/μm | Target | Range |
| <10 | 11.0 | 8-13.5 |
| <30 | 17.5 | 10-25 |
| <60 | 31.0 | 20-42 |
| <90 | 45.0 | 30-60 |

TABLE 1-continued

Particle size distributions for carrier lactose.
Median of particle size distribution must be in the range of 70-120 μm.

| Size/μm | % Cumulative Undersize | |
|---|---|---|
|  | Target | Range |
| <174 | <90 | — |
| <250 | 100 | — |

The inhalers that contained the formulation were then tested for pharmaceutical performance under conditions specified in European Pharmacopoeia (2001) including uniformity of delivered dose and fine particle dose. The drug per actuation (DPA) was measured using a dose unit sampling unit in conjunction with a critical flow controller model TPK, high capacity pump and flowmeter (Copley Scientific, Nottingham, U.K.) while fine particle dose (FPD) and fine particle fraction (FPF) were measured using a 5-stage liquid impinger MSL also from Copley Scientific.

The compositions gave excellent dose uniformity with relative standard deviation (RSD) of delivered doses ranging from 4-13% (Table 2) when used in association with the IVAX™ MDPI device, with a good proportion of fine particles of the drug (Table 3). The pharmaceutical performance of the inhalers remains stable after unprotected exposure to elevated storage conditions.

TABLE 2

Relative standard deviation (RSD) of ten doses (3 at beginning, 4 at middle and 3 at end of device life) from each inhaler device containing a formulation using the said lactose as the excipient before and after storage unprotected at 25° C./60% RH for a month.

| Before storage | | | After storage | | |
|---|---|---|---|---|---|
| Device 1 | Device 2 | Device 3 | Device 1 | Device 2 | Device 3 |
| 8.1% | 7.9% | 11.4% | 12.8% | 10.5% | 4.7% |

TABLE 3

Fine particle fraction (FPF, % recovered dose) of formoterol from each inhaler device containing a formulation using the said lactose as excipient before and after storage unwrapped at 25° C./60% RH for a month.

| Parameters | Before storage | | | After storage | | |
|---|---|---|---|---|---|---|
|  | Device 1 | Device 2 | Device 3 | Device 1 | Device 2 | Device 3 |
| Beginning of device life | 38 | 40 | 40 | 41 | 39 | 39 |
| End of device life | 38 | 38 | 42 | 40 | 35 | 43 |

Example 2

Particle Size Distribution for a Formoterol Lactose Blend 0.265 grams of formoterol (as the fumarate dihydrate salt) was blended according to the methods of Example 1, with 99.735 grams of lactose that has a particle size distribution within the range as shown in Table 4. The lactose was prepared by blending a mixture of 90 to 150 micron lactose (95%) with microfine lactose having a VMD of 7.5 microns (5%). The formoterol lactose blend was filled into the reservoir of an IVAX™ MDPI dry powder inhaler. A typical particle size distribution for a lactose blend thus prepared is shown in FIG. 1.

TABLE 4

Particle size distribution for the formoterol lactose blend

| Parameters | Mean | Range |
|---|---|---|
| VMD | 97 μm | 89-110 μm |
| GSD | 4.4 | 2.2-4.9 |
| <5 μm | 13.1% | 8.0%-24.0% |
| <10 μm | 21.6% | 14.2%-28.5% |
| <15 μm | 24.5% | 15.0%-31.0% |
| <30 μm | 26.5% | 16.0%-34.0% |
| <60 μm | 29.6% | 18.9%-36.1% |
| <90 μm | 44.5% | 34.8%-50.8% |
| <150 μm | 87.7% | 83.9%-93.5% |
| <174 μm | 96.0% | 93.8%-98.9% |
| <250 μm | 100% | 100% |

Example 3

Formoterol Deposition Profile Determinations

In order to measure the performance of the product thus developed, a study was undertaken which compared the drug delivery and deposition properties of the compositions of the invention from, for example, an IVAX™ MDPI device with a representative commercial product, the OXIS TURBUHALER™ (AstraZeneca Pharmaceuticals, U.K., label claim 6 mcg, formoterol per dose). The IVAX™ MDPIs and OXIS TURBUHALERS® were tested under the same conditions specified in European Pharmacopoeia (2001). The drug per actuation (DPA) was measured using a dose unit sampling apparatus while fine particle dose (FPD) and fine particle fraction (FPF) were measured using a 5-stage liquid impinger as per Example 1.

Figure 2:
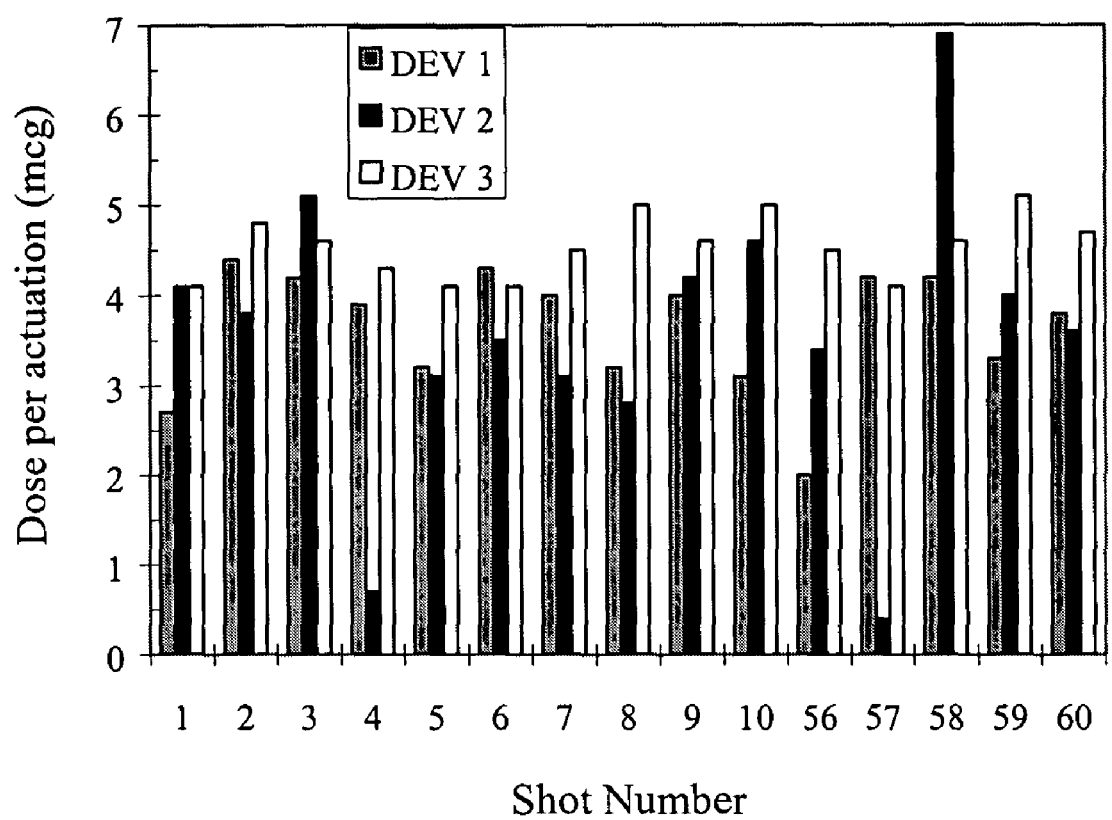
FIG. 2: Graphical representation of drug per actuation from a representative commercial product with a label claim of 6 µg formoterol (OXIS TURBUHALER™, Batch ZE226).
Figure 3:
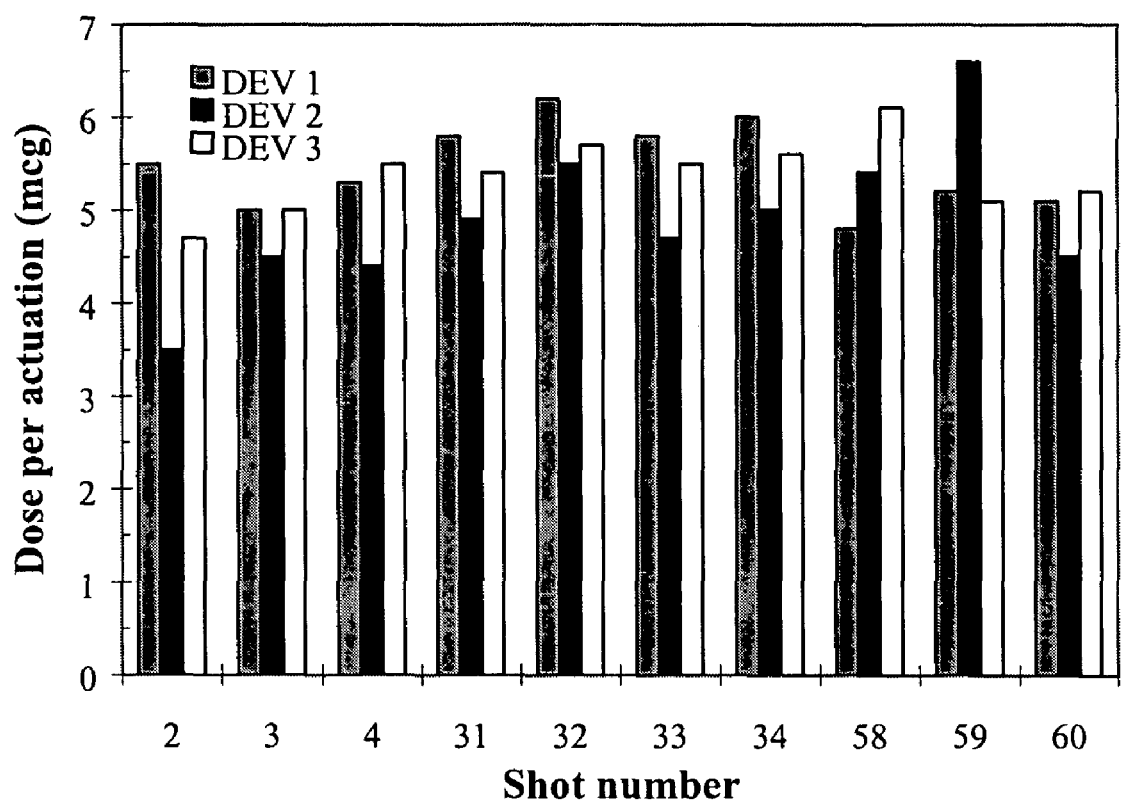
FIG. 3: Graphical representation of drug delivery per actuation from an IVAX™ MDPI with a label claim of 6 µg.

The commercial product (FIG. 2) showed a larger variation in DPA than the compositions as used with an IVAX™ MDPI (FIG. 3). The mean DPA from three commercial products (with label claim of 6 μg) was 3.9 μg, suggesting that a large portion (over 30%) of the drug was not released from the device. The mean DPA from three IVAX MDPIs was 5.3 μg, (within 80-120% of the label claim of 6 μg). The three commercial devices showed an RSD of 27.8% for the DPA values which was more than twice the value (11.9%) of the IVAX™ MDPI, indicating a more consistent delivery of drug.

No significant difference was found in the fine particle dose (FPD) of formoterol from the IVAX™ MDPI (2.37±0.19 μg) and the representative commercial (2.27±0.39 μg) (See Table 5).

TABLE 5

Deposition profiles of formoterol from a representative commercial product (OXIS TURBUHALER ™) and an IVAX ™ MDPI (The label claim of both devices was 6 μg)

| | IVAX ™ MDPI | | | OXIS TURBUHALER ™ (batch ZE 226) | | |
|---|---|---|---|---|---|---|
| | Device 1 | Device 2 | Device 3 | Device 1 | Device 2 | Device 3 |
| Actuations 7-26 | | | | | | |
| IND. PORT (μg) | 1.07 | 1.12 | 0.98 | 1.00 | 1.00 | 1.10 |
| STAGE 1(μg) | 1.95 | 1.94 | 1.94 | 0.20 | 0.10 | 0.20 |
| STAGE 2(μg) | 0.39 | 0.24 | 0.29 | 0.10 | 0.10 | 0.20 |
| STAGE 3(μg) | 0.82 | 0.77 | 0.83 | 0.60 | 0.70 | 0.90 |
| STAGE 4(μg) | 0.83 | 0.90 | 0.82 | 0.90 | 0.90 | 1.10 |
| STAGE 5(μg) | 0.73 | 0.78 | 0.65 | 0.70 | 0.70 | 0.90 |
| RD (μg) | 5.79 | 5.75 | 5.51 | 3.50 | 3.50 | 4.20 |
| FPD (μg) | 2.60 | 2.50 | 2.40 | 2.30 | 2.30 | 2.80 |
| FPF (% RD) | 45 | 43 | 44 | 66 | 66 | 67 |
| FPF (% LC) | 43 | 42 | 40 | 38 | 38 | 47 |
| Actuations 35-56 | | | | | | |
| IND. PORT (μg) | 0.93 | 0.83 | 0.85 | 1.10 | 0.90 | 0.70 |
| STAGE 1(μg) | 2.16 | 2.08 | 2.15 | 0.30 | 0.20 | 0.20 |
| STAGE 2(μg) | 0.25 | 0.27 | 0.26 | 0.10 | 0.10 | 0.20 |
| STAGE 3(μg) | 0.64 | 0.72 | 0.67 | 0.70 | 0.60 | 0.50 |
| STAGE 4(μg) | 0.71 | 0.84 | 0.76 | 0.90 | 0.80 | 0.60 |
| STAGE 5(μg) | 0.60 | 0.76 | 0.71 | 0.70 | 0.70 | 0.50 |
| RD (μg) | 5.29 | 5.50 | 5.40 | 3.90 | 3.40 | 2.60 |
| FPD (μg) | 2.10 | 2.40 | 2.20 | 2.40 | 2.20 | 1.60 |
| FPF (% RD) | 40 | 44 | 41 | 62 | 65 | 62 |
| FPF (% LC) | 35 | 40 | 37 | 40 | 37 | 27 |

Note:
RD is the total recovered dose from the impinger; LC is label claim and IND. Port stands for Induction Port.

Example 4

Consistency of Formoterol Delivery

A blend composed of 0.26% w/w micronized formoterol in the lactose was prepared as previously described. The final products were found to produce a mean drug per actuation within 80-120% label claim, mean fine particle dose expressed as percentage of label claim >37%. All parameters met Pharmacopoeial specifications set up for dry powder inhalers, previously cited. The fine particle dose for the composition when used in conjunction with an IVAX™ MDPI, which relates directly to the therapeutic equivalence of these inhalers, was comparable to the representative commercial product. Delivery of the composition of the invention with an IVAX™ MDPI was shown to be more consistent in the delivery of formoterol than the commercial product. (Data not shown)

Example 5

Preparation of Medicament Blends

A blend of micronized medicament chosen from a group consisting of, but not limited to, bronchodilators (e.g., epinephrine, metaproterenol, terbutaline, albuterol, and the like), anticholinergic agents (e.g., ipratropium bromide), xanthines (e.g., aminophylline, dyphylline, aminophylline), inhalant corticosteroids (e.g., flunisolide, beclomethasone, budesonide, and the like), or β-2 adrenergic receptor agonists (e.g., salmeterol) is blended with lactose according to the methods described in Example 1. The resulting blend is introduced into an IVAX™ MDPI and then tested for pharmaceutical performance under the conditions specified in European Pharmacopoeia. The drug per actuation (DPA) is measured using a dose unit sampling unit while fine particle dose (FPD) and fine particle fraction (FPF) are measured using a 5-stage liquid impinger as previously described.

EQUIVALENTS

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:
1. A dry powder inhalation composition comprising,
   (a) medicament particles, and
   (b) a mixture of lactose particles with a volume mean diameter (VMD) of between about 70 and about 120 microns and a diameter of less than 250 microns, wherein up to 96% by weight of the lactose particles are less than 150 microns in diameter and wherein up to 25% by weight of the lactose particles are less than 5 microns in diameter.
2. A dry powder inhalation composition according to claim 1, wherein up to 85% by weight of the lactose particles are less than 90 microns in diameter.
3. A dry powder inhalation composition according to claim 1, wherein up to 37% by weight of the lactose particles are less than 60 microns in diameter.

4. A dry powder inhalation composition according to claim 1, wherein up to 35% by weight of the lactose particles are less than 30 microns in diameter.

5. A dry powder inhalation composition according to claim 1, wherein up to 31.5% by weight of the lactose particles are less than 15 microns in diameter.

6. A dry powder inhalation composition according to claim 1, wherein up to 30% by weight of the lactose particles are less than 10 microns in diameter.

7. A dry powder inhalation composition according to claim 1, wherein between 6.5 and 24.5% by weight of the lactose particles are less than 5 microns in diameter.

8. A dry powder inhalation composition according to claim 1 or 7, comprising up to 10% by weight of medicament particles.

9. A dry powder inhalation composition according to claim 1, wherein the medicament particles are formoterol or a pharmaceutically acceptable salt, hydrate or salt hydrate thereof.

10. A dry powder inhalation composition according to claim 1, wherein the medicament particles are formoterol fumarate dihydrate.

11. The dry powder inhalation composition of claim 1, wherein said mixture of lactose particles is characterized by the particle size distribution of the following table

| Parameters | Mean | Range |
|---|---|---|
| VMD | 97 im | 89-110 |
| GSD | 4.4 | 2.2-4.9 |
| <5 μm | 13.1% | 8.0%-24.0% |
| <10 μm | 21.6% | 14.2%-28.5% |
| <15 μm | 24.5% | 15.0%-31.0% |
| <30 μm | 26.5% | 16.0%-34.0% |
| <60 μm | 29.6% | 18.9%-36.1% |
| <90 μm | 44.5% | 34.8%-50.8% |
| <150 μm | 87.7% | 83.9%-93.5%. |
| <174 μm | 96.0% | 93.8%-98.9% |
| <250 μm | 100% | 100%. |

12. A multidose dry powder inhaler comprising a dry powder inhalation composition according to claim 1.

13. A dry powder inhalation composition comprising,
(a) medicament particles, and
(b) a mixture of lactose particles characterized by the particle size distribution of the following table

| | % Cumulative Undersize | |
|---|---|---|
| Size/gm | Target | Range |
| <10 | 11.0 | 8-13.5 |
| <30 | 17.5 | 10-25 |
| <60 | 31.0 | 20-42 |
| <90 | 45.0 | 30-60 |
| <174 | >90 | — |
| <250 | 100 | — |

14. A method for the administration of a particulate medicament, comprising inhalation from a multidose dry powder inhaler of a dry powder inhalation composition according to claim 1.

15. A method for making the composition of claim 1 comprising the steps of
a) blending a portion of fine lactose particles and a portion of coarse lactose particles, wherein said portion of fine lactose particles has a mean particle diameter of less than 10 microns, and wherein said portion of coarse lactose particles is prepared by a method comprising collecting lactose particles on a mesh with mesh size of 63 microns after passing through a mesh with mesh size of 90 microns, to obtain the mixture of lactose particles, and b) blending the mixture of lactose particles with medicament particles.

* * * * *